US010179203B1

(12) United States Patent
Huslage

(10) Patent No.: US 10,179,203 B1
(45) Date of Patent: Jan. 15, 2019

(54) INTRAVENOUS (IV) SITE AND MEDICAL TUBING PROTECTION UTILIZING RETRACTABLE SPOOL SYSTEM AND ASSOCIATED USE THEREOF

(71) Applicant: Kathy McArthur Huslage, Baltimore, MD (US)

(72) Inventor: Kathy McArthur Huslage, Baltimore, MD (US)

( * ) Notice: Subject to any disclaimer, the term of this patent is extended or adjusted under 35 U.S.C. 154(b) by 462 days.

(21) Appl. No.: 15/085,133

(22) Filed: Mar. 30, 2016

(51) Int. Cl.
*A61M 5/14* (2006.01)
*A61M 39/08* (2006.01)
*A61M 39/10* (2006.01)
*A61M 5/168* (2006.01)

(52) U.S. Cl.
CPC ...... *A61M 5/1415* (2013.01); *A61M 5/16813* (2013.01); *A61M 39/08* (2013.01); *A61M 39/10* (2013.01); *A61M 2005/1416* (2013.01)

(58) Field of Classification Search
CPC ............ A61M 5/1415; A61M 5/16813; A61M 2005/1416; A61M 25/02; A61M 39/1055; A61M 2039/1072; A61M 2039/0229; A61M 39/08; A61M 39/10; B65H 75/4452; Y10T 137/6929
See application file for complete search history.

(56) References Cited

U.S. PATENT DOCUMENTS

| | | | | | |
|---|---|---|---|---|---|
| 3,194,235 | A | * | 7/1965 | Cooke | A61M 25/02 128/888 |
| 4,543,982 | A | * | 10/1985 | Wolfe | B65H 75/40 137/355.21 |
| 4,713,059 | A | * | 12/1987 | Bickelhaupt | A61M 25/0113 242/588.6 |
| 4,846,807 | A | * | 7/1989 | Safadago | A61M 5/158 604/179 |
| 4,913,369 | A | * | 4/1990 | Lia | B65H 75/40 242/129 |
| 5,112,313 | A | * | 5/1992 | Sallee | A61M 25/0612 604/180 |
| 5,116,324 | A | * | 5/1992 | Brierley | A61M 25/02 128/DIG. 6 |
| 5,236,143 | A | * | 8/1993 | Dragon | B65H 75/48 226/187 |
| 5,265,822 | A | * | 11/1993 | Shober, Jr. | A61M 5/1418 242/388.2 |

(Continued)

Primary Examiner — Matthew F Desanto

(57) ABSTRACT

An intravenous (IV) site and medical tubing protection device which diminishes the inadvertent, non-purposeful dislodging of an IV catheter, as fluids are being delivered to a patient via a medicine dispensing unit. It employs a self-contained retractable spring spool unit consisting of medicinal tubing 13, a spring-loaded, retractable spool 8, an IV Luer 5, a lubricating ring port 9, a swiveling fluid junction 10, bolus valve 11, and a plastic shell container 7. Medicinal tubing 13 enters the plastic shell container 7 through a lubricating ring port 9 and winds around the retractable spool 8. The tubing attaches to a swiveling fluid junction 10, which permits a constant flow of fluid through the patient line, despite any extending or retracting of the tubing. A subsequent patient line attaches to the swiveling fluid junction 10 at its other end and then to an IV luer 5 that extends beyond the plastic shell 7. An IV catheter can then be attached to the luer 5.

1 Claim, 4 Drawing Sheets

Concept-Component Overview

Concept-Cross sections

(56) References Cited

U.S. PATENT DOCUMENTS

| | | | | |
|---|---|---|---|---|
| 5,975,120 | A * | 11/1999 | Novosel | A61M 16/0666 137/355.23 |
| 6,588,444 | B2 * | 7/2003 | Paplow | B65H 75/40 137/15.01 |
| 6,889,688 | B1 * | 5/2005 | Wright | B65H 75/406 128/200.24 |
| 6,949,084 | B2 * | 9/2005 | Marggi | A61M 25/0097 604/174 |
| 7,216,665 | B1 * | 5/2007 | Sims, Jr. | A61M 39/08 137/355.19 |
| 7,654,484 | B2 * | 2/2010 | Mogensen | A61M 5/1418 242/402 |
| 7,805,849 | B1 * | 10/2010 | Baker, Jr. | G01C 9/34 33/1 LE |
| 8,500,054 | B2 * | 8/2013 | Grant | A61M 5/1418 242/388.1 |
| 8,746,246 | B2 * | 6/2014 | Lueckenhoff | A61M 16/0875 128/204.18 |
| 2003/0122021 | A1 * | 7/2003 | McConnell | A61M 39/08 242/388.1 |
| 2003/0146332 | A1 * | 8/2003 | Vinding | A61M 39/08 242/378.4 |
| 2005/0234423 | A1 * | 10/2005 | Mogensen | A61M 39/08 604/500 |
| 2009/0277454 | A1 * | 11/2009 | Davis | A61M 16/0875 128/207.18 |
| 2011/0017856 | A1 * | 1/2011 | Penn | A61M 39/08 242/370 |
| 2013/0030348 | A1 * | 1/2013 | Lauer | A61M 5/1407 604/6.16 |
| 2013/0178836 | A1 * | 7/2013 | Teutsch | A61M 39/08 604/533 |
| 2015/0069164 | A1 * | 3/2015 | Moore | B65H 75/4434 242/382 |

* cited by examiner

Concept-Function Overview

Concept–Component Overview

Alternate Concept – Breakaway

INTRAVENOUS (IV) SITE AND MEDICAL TUBING PROTECTION UTILIZING RETRACTABLE SPOOL SYSTEM AND ASSOCIATED USE THEREOF

CROSS REFERENCE TO RELATED APPLICATIONS

Not Applicable.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE DISCLOSURE

Technical Field

This disclosure relates to Intravenous (IV) tubing and, more particularly, to a retractable spool system which prevents the unintentional dislodging of IV tubes and IV catheter sites that deliver medicine and other desired contents to a patient.

Prior Art

The following is a tabulation of some prior art that presently appears relevant:

| Cited Patent | Filing date | Publication date | Applicant | Title |
|---|---|---|---|---|
| U.S. Pat. No. 4,666,111 | Nov. 14, 1985 | May 19, 1987 | Robert Schuler | Holder for IV tube |
| U.S. Pat. No. 4,846,807 | Feb. 26, 1988 | Jul. 11, 1989 | Safadago Gary J | IV tube anchor and shield |
| U.S. Pat. No. 4,857,058 A | Jul. 11, 1988 | Aug. 15, 1989 | Payton Hugh W. | Support patch for IV catheter |
| U.S. Pat. No. 5,810,781 | Feb. 14, 1996 | Sep. 22, 1998 | Venetec International, Inc. | Catheter fitting securement device |
| U.S. Pat. No. 5,832,928 A | Apr. 8, 1997 | Nov. 10, 1998 | James D. Padilla, Jr. | Intravenous site protection device |
| U.S. 20070106222 A1 | Oct. 24, 2005 | May 10, 2007 | Tionne Bennett | Intravenous site protective cover |
| U.S. 20110040258 A1 | Jul. 28, 2010 | Feb. 17, 2011 | Carroll V. Robison | Flexible and adjustable wrap for protecting and stabilizing IV catheter |
| U.S. Pat. No. 8,834,426 B2 | May 24, 2011 | Sep. 16, 2014 | Russell Shipman | Catheter and tubing restraining device and protective cover |
| U.S. 20130150796 A1 | Dec. 5, 2012 | Jun. 13, 2013 | Marcel A. Souza | Foldable IV cath secure |

In the medical field, it is common practice to supply blood and other fluids to the patient intravenously. Standard intravenous supply devices include an intravenous catheter penetrating the skin, coupled via IV luer to a supply tube. The medicinal supply tube is typically connected to a supply bag or pouch, from which the contents are introduced to the patient via gravity or, alternatively, connected to a standard infusion pump to provide a more accurate and controlled rate of flow through the IV tube.

The standard supply tube is formed from a pliable clear plastic material that is easily twisted and handled. The nature of the tubing makes it easy for patients to grip and pull it, and potentially dislodging its attached IV site. This is especially true for patients who are delirious, demented, or otherwise cognitively impaired and do not understand the medical benefits of the IV delivery system. Their unintentional grasping at the IV tubing can lead to removal of the IV catheter and the cessation of necessary fluids to the body.

There is therefore a need for a system which is able to reduce the risks of involuntary dislodging or removal of an intravenous supply system without interfering with the flow of fluids therein or creating other undesirable effects.

Previous art focused on the direct securement of medicinal tubing to the patient's skin. It employed various taping procedures and locking devices meant to create a deterrent to accidental removal of both IV tubing and catheter by patient or staff. For patients who are of sound mind and understand the medical advantages of an IV, such deterrents are satisfactory. For patients who are demented, delirious, or otherwise cognitively impaired, taping procedures and locking devices have proven insufficiently preventative. With sufficient attention to and manipulation of the tubing and IV site, patients can downgrade the integrity of the IV site, requiring undue nursing attention and increasing the chances of infection.

Advantages

The introduction of a device which allows for patient manipulation of an IV line without disturbing the integrity of the IV system (the flow of liquids into a patient) is seen as a clear improvement in the art. Patients who are demented, delirious, or some other way cognitively impaired will frequently pull at tubing and other medical paraphernalia, as they perceive them to be foreign and uncomfortable objects. A device that would allow IV tubing to be repeatedly pulled without dislodging the IV site will significantly reduce IV reinsertion rates, nursing-patient interactions with patients, and infection rates associated with unintended IV removal. Unintentional IV removal also discontinues the medically-necessary fluids from entering the patient, creates spillage of fluids and need for clean-up, and diminishes skin integrity at the IV site. For these reasons, medical settings will frequently hire professional sitters to monitor a patient, incurring financial cost to the medical setting. So, in summary, the advantages of this embodiment include long-term integrity of the IV line and catheter insertion site, reduced re-insertion rates, reduced. Infections, and cost savings to the medical setting.

BRIEF SUMMARY OF THE DISCLOSURE

In view of the foregoing background, it is therefore an object of the non-limiting exemplary embodiments to provide a retractable spring spool system to ensure a patient continuously receives medication via IV for an extended period of time. These and other objects, features and advantages of the disclosure are provided by a medicine delivering tube capable of transporting fluid from an existing medicine dispensing unit to the patient and a self-contained retractable spring spool unit consisting of medicinal tubing, a spring-loaded retractable spool, an IV luer, a lubricating ring port, a swiveling fluid junction and a plastic shell container.

The internal components of the embodiment are contained in a protective plastic shell container, which low profile design makes the device difficult to grip. The shell cover is held in place by an adhesive ring which runs the circumference of the shell cover.

The embodiment is employed in concert with standard medical tubing and IV protocols. Entering the device is 3-4 feet of medical tubing which originates from a medicine or blood dispensing unit from which fluid is transported through the embodiment to the IV site and into the patient's body.

In a non-limiting exemplary embodiment, the tubing enters the embodiment's protective plastic shell and coils around the spring loaded spool. The spool can release up to two feet of tubing, if pulled by a force of some kind. When released, it will retract back into the shell and around the spool.

In a non-limiting exemplary embodiment, a lubricating ring port is located where the medicinal tube enters the device shell. The lubricator has two functions; specifically, to create a smooth reeling out of the tubing from the spool and to make the extended tubing less able to be grasped by the patient's hand.

In a non-limiting exemplary embodiment, the spring spool unit contains a swiveling fluid junction. The junction permits a constant flow of fluid through the patient line, despite the extending and retracting of the tubing. The patient line attaches to the swiveling fluid junction at its one end and to the IV luer at the other.

There has thus been broadly outlined the more salient features of the disclosure in order that the detailed description thereof that follows may be better understood, and in order that the present contribution to the art may be better appreciated. There are additional features of the disclosure that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly form a cursory inspection the nature and essence of the technical disclosure of the application. The abstract is neither intended to define the disclosure of the application, which is measured by the claims, nor is it intended to be limiting as to the scope of the disclosure in any way.

BRIEF DESCRIPTION OF THE SEVERAL VIEWS OF THE DRAWING

The novel features believed to be characteristic of this disclosure are set forth with particularity in the appended claims. The disclosure itself, however, both as to its organization and method of operation, together with further objects and advantages thereof, may best be understood by reference to the following description taken in connection with the accompanying drawings in which:

DETAILED DESCRIPTION OF THE DISCLOSURE/SPECIFICATIONS

Figure 1:
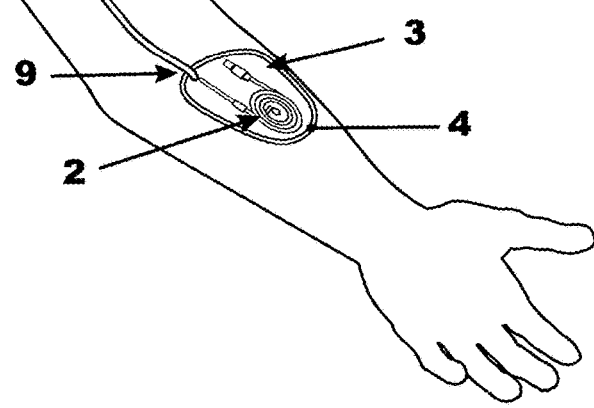
FIG. 1. Is a concept/functional overview of the device. It shows the basic mechanism as it would appear on a patient's body in a medical environment, in accordance with the device description in subsequent sections.

The non-limiting exemplary embodiments will now be described more fully hereinafter with reference to the accompanying drawings, in which a preferred embodiment of the disclosure is shown. This disclosure may, however, be embodied in many different forms and should not be construed as limited to the embodiment set forth herein. Rather, this embodiment is provided so that this application will be thorough and complete, and will fully convey the true scope of the disclosure to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of system and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "non-limiting exemplary embodiments" merely for convenience and without intending to voluntarily limit the scope of this application to any particular disclosure or inventive concept. Moreover, although specific embodiments have been illustrated and described herein, it should be appreciated that any subsequent arrangement designed to achieve the same or similar purpose may be substituted for the specific embodiments shown. This disclosure. Is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. .sctn.1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own subject matter.

The below disclosed subject matter is to be considered illustrative, and not restrictive, and the appended claims are intended to cover all such modifications, enhancements, and other embodiments which fall within the true scope of the non-limiting exemplary embodiments. Thus, to the maximum extent allowed by law, the scope of the non-limiting exemplary embodiments is to be determined by the broadest permissible interpretation of the following claims and their equivalents, and shall not be restricted or limited by the foregoing detailed description.

Figure 2:
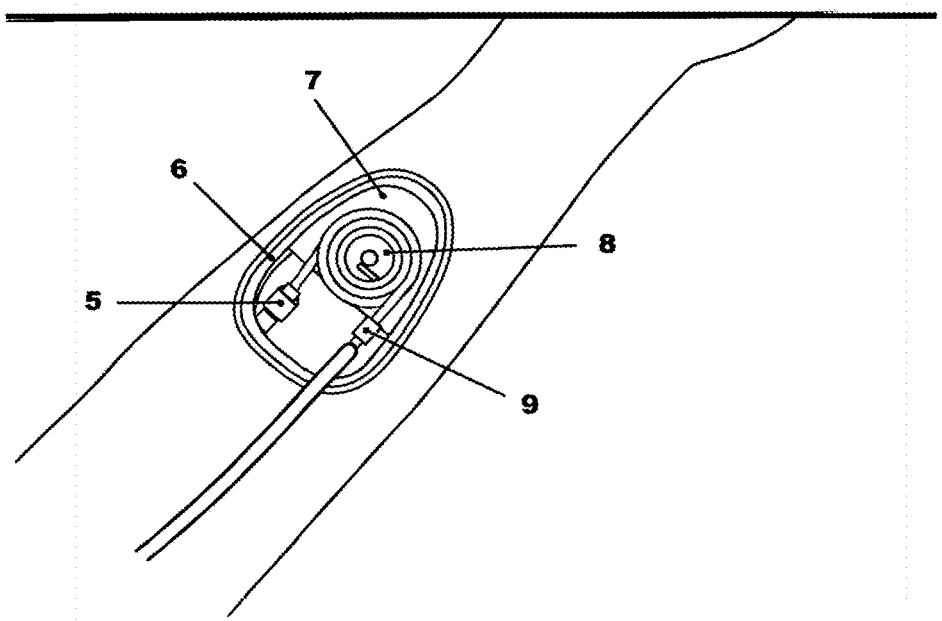
FIG. 2. Is a component overview showing the elements and internal device mechanisms, including the retractable spool, lubricating ring port, adhesive strip and IV luer.
Figure 3:
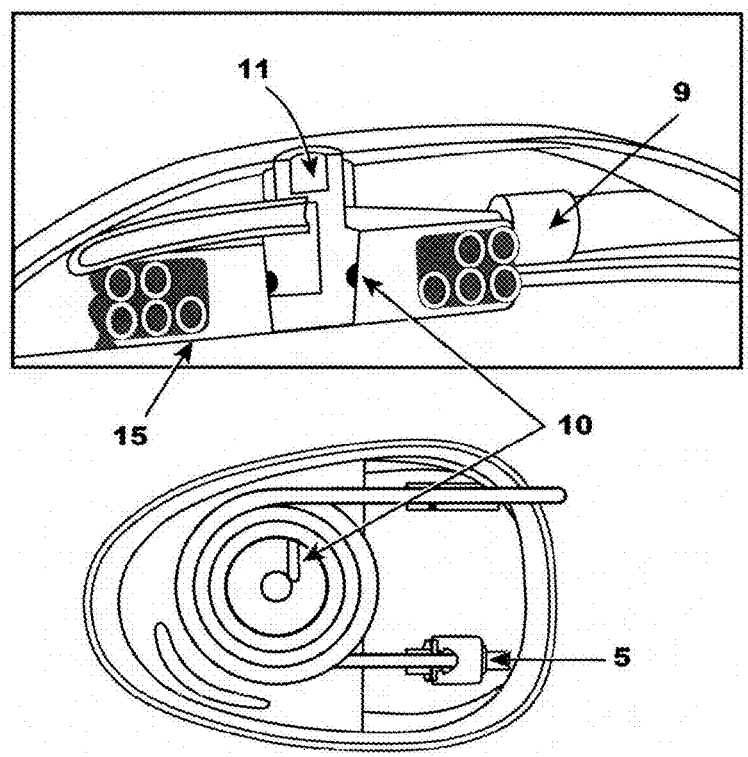
FIG. 3. Is a cross section view of the device, showing the internal working of the device, including the retractor mechanism, tubing lubricator and alternative bolus valve.
Figure 4:
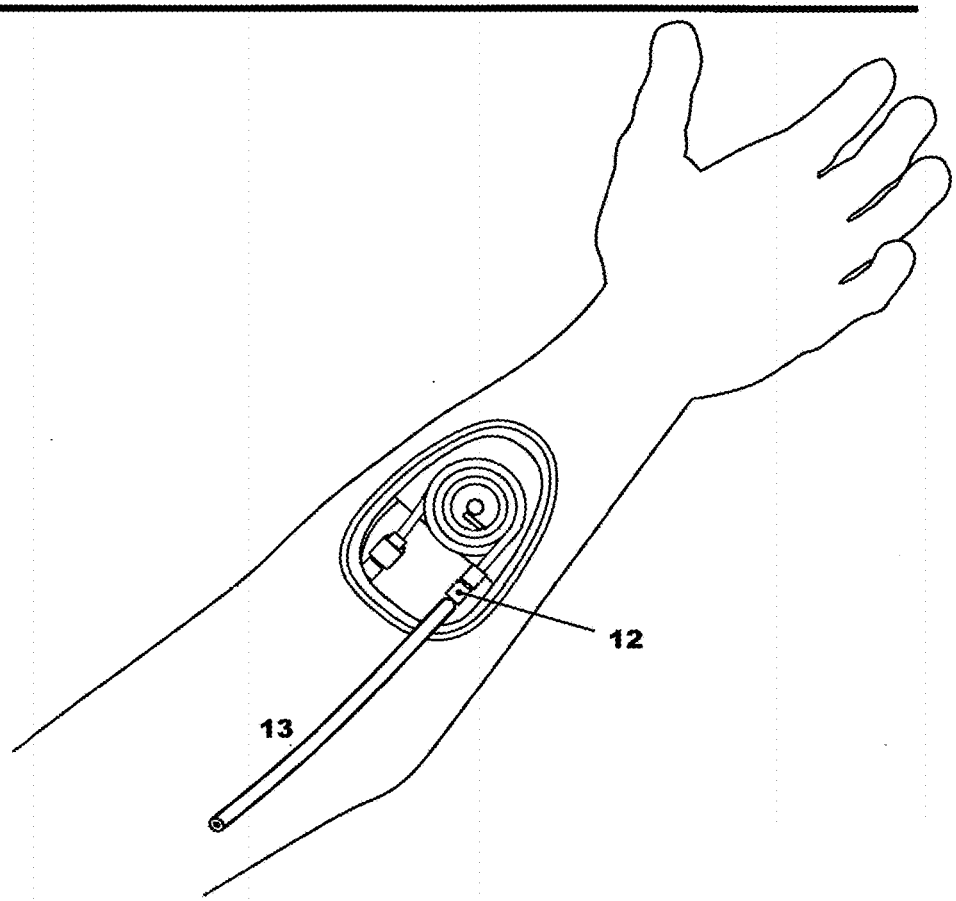
FIG. 4. Shows an alternative breakaway concept, described in the disclosure.

The system of this disclosure is referred to generally in FIGS. 1-4 and is intended to provide a medicinal tubing protection system utilizing a retractable spring spool. It should be understood that the present disclosure may be used to prevent patients from accidentally or non-purposefully pulling out an intravenous tube (medicine delivering tube) and related atheter site in many different types of medical and other situations, and should not be limited to the uses described herein.

Referring to FIGS. 1-4, in general, an object of the non-limiting exemplary embodiments provides a retractable spring spool system to ensure a patient continuously receives medication and other fluids via IV for an extended period of time. These and other objects, features and advantages of the disclosure are provided by a medicine delivering tube 13 capable of transporting fluid from an existing medicine dispensing unit to the patient and a self-contained retractable spring spool unit consisting of medicinal tubing 13, a spring-loaded, retractable spool 8, an IV Luer 5, a lubricating ring port 9, a swiveling fluid junction 10, bolus valve 11, and a plastic shell container 7. The construction of the embodiment will allow for the separate elements of the device to work freely and as designed by maintaining minimal friction between the moving and stationary parts.

The internal components of the embodiment (spring-loaded, retractable spool 8, IV Luer 5, lubricating ring port 9, swiveling fluid junction 10, and bolus valve 11) are contained in a protective plastic shell cover 7, whose low profile design 3 makes the device unobtrusive and difficult to grip. Other methods such as a form-fitting arm sleeve may be used to obscure the shell cover, as well. The shell cover is affixed in place by an adhesive ring 4 which runs the entire circumference of the shell cover, except where the IV luer 5 exits the device. Alternatively, the shell can be affixed to the body using other sanctioned methods already available in the medical device marketplace.

The basic working of the device is as follows: The embodiment works in conjunction with already established IV protocols related to the provision of fluids, blood or medicine via medical tubing as prescribed for a patient. The embodiment is attached to the patient at a medically appropriate point between the patient line and the IV catheter insertion site. The ability of the device to accommodate the non-purposeful or accidental pulling of the IV tube by a person serves as an effective means of maintaining IV system integrity.

The spring spool embodiment is employed in concert with typical medical tubing and IV protocols. Entering plastic shell 7 is 3-4 feet of medical tubing 13, which is an element of the embodiment. The tubing is attached to any standard medicine or blood infusion unit from which fluid is transported through the embodiment to the IV site and into the patient's body.

In a non-limiting exemplary embodiment, the tubing 13 enters the protective plastic shell 7 of the device and coils around the retractable spool 8. At the entrance of the shell 7, the tube passes through a lubricating ring port 9, capable of emitting antimicrobial lubricant to the tube, if it is pulled away from the device. The lubricating ring port 9 has two functions; specifically, to create a smooth reeling out of the tubing 13 from the spool 8 through the shell opening 12 and to make the extended tubing less able to be grasped by the patient's hand.

In a non-limiting exemplary embodiment, the retractable spool 8 can release up to two feet of tubing, if pulled by a force of some kind. When the pulling force stops, the tubing will retract back into the shell 7 and around the spool 8. The design of the spool will allow the tubing to recoil in such a way that it does not bind, entangle or snag. The spring tension of the retraction spool 8 will be set to assure full retraction, while not interfering with the IV process and flow of liquids.

In a non-limiting exemplary embodiment, the embodiment contains a swiveling fluid junction 10. The junction permits the constant flow of liquid or blood through the patient line 13 and the IV luer 5 to remain stationary, notwithstanding the pulling and retraction of the tubing. The patient line attaches to the swiveling fluid junction 10 at its one end and to the IV luer 5 at the other. Per the embodiment design, the IV luer 5 is placed outside of the shell 7 exterior, allowing an inserted IV catheter to be easily attached.

An alternative element is the inclusion of a breakaway valve 12 at the point where the medical tubing 13 enters the shell cover. If the IV tubing 13 is pulled beyond a predetermined force, the valve 12 will separate and both sides of the line will automatically close. This protects from damage to the IV line 13 and the IV luer 5 and catheter, as well as preventing fluid leakage.

There has thus been broadly outlined the more salient features of the disclosure in order that the detailed description thereof that follows may be better understood, and in order that the present contribution to the art may be better appreciated. There are additional features of the disclosure that will be described hereinafter and which will form the subject matter of the claims appended hereto.

CONCLUSION, RAMIFICATIONS AND SCOPE

It is clear from the above description that the embodiment will serve as a substantive means to reduce the inadvertent and non-purposeful removal of IV tubing and related catheter sites in numerous medical situations and especially with cognitively impaired patients. It will maintain the integrity of the Intravenous system, reducing the need for more restrictive or expensive measures to maintain said integrity. IV line integrity leads to reduced medical complications, decreased infection and improved patient outcomes. While the disclosure has been described with respect to a certain specific embodiment, it will be appreciated that many modifications and changes may be made by those skilled in the art without departing from the spirit of the disclosure. It is intended, therefore, by the appended claims to cover all such modifications and changes as fall within the true spirit and scope of the disclosure. In particular, with respect to the above description, it is to be realized that the optimum dimensional relationship for the parts of the non-limiting exemplary embodiments may include variations in size, materials, shape, form, function and manner of operation.

It is noted the purpose of the foregoing abstract is to enable the U.S. Patent and Trademark Office and the public generally, especially the scientists, engineers and practitioners in the art who are not familiar with patent or legal terms or phraseology, to determine quickly form a cursory inspection the nature and essence of the technical disclosure of the application. The abstract is neither intended to define the disclosure of the application, which is measured by the claims, nor is it intended to be limiting as to the scope of the disclosure in any way.

What is claimed is:

1. An IV site protection device, comprising;
   a plastic shell cover having a circular opening with a lubricant ring port located at said circular opening;

a medical tubing;

a retractable spring spool mechanism capable of releasing and retracting said medical tubing;

a swiveling fluid junction conjoined to said retractable spring spool mechanism to allow fluids or substances to continuously pass through said medical tubing;

a bolus valve incorporated into said swiveling fluid junction;

an IV tube with a first end attached to said swiveling fluid junction and a second end attached to an IV luer;

wherein said medical tubing is configured to be attached to an IV line from a fluid dispenser or infusion unit, and when said medical tubing is pulled in and out of said circular opening, said medical tubing is lubricated by said lubricating ring port.

\* \* \* \* \*